(12) United States Patent
Dalmia et al.

(10) Patent No.: US 6,908,537 B2
(45) Date of Patent: Jun. 21, 2005

(54) ELECTROCHEMICAL SENSORS HAVING NONPOROUS WORKING ELECTRODE

(75) Inventors: Avinash Dalmia, Hamden, CT (US); Otto J. Prohaska, Seymour, CT (US)

(73) Assignee: PerkinElmer Instruments LLC, Shelton, CT (US)

( * ) Notice: Subject to any disclaimer, the term of this patent is extended or adjusted under 35 U.S.C. 154(b) by 180 days.

(21) Appl. No.: 10/029,507

(22) Filed: Oct. 22, 2001

(65) Prior Publication Data

US 2003/0075442 A1 Apr. 24, 2003

(51) Int. Cl.[7] .............................................. G01N 27/407
(52) U.S. Cl. ...................................... 204/424; 204/426
(58) Field of Search .................................. 204/421–429

(56) References Cited

U.S. PATENT DOCUMENTS

| | | | |
|---|---|---|---|
| 4,343,177 A | | 8/1982 | Carlon et al. |
| 4,878,015 A | | 10/1989 | Schmidt et al. |
| 4,896,143 A | | 1/1990 | Dolnick et al. |
| 4,900,405 A | * | 2/1990 | Otagawa et al. |
| 5,164,053 A | * | 11/1992 | Razaq et al. |
| 5,298,783 A | | 3/1994 | Wu |
| 5,716,506 A | | 2/1998 | Maclay et al. |
| 5,762,770 A | * | 6/1998 | Pritchard et al. ...... 204/403.14 |
| 5,987,964 A | | 11/1999 | Miremadi |
| 5,989,409 A | * | 11/1999 | Kurnik et al. ............... 205/792 |
| 6,029,500 A | | 2/2000 | Tom |
| 6,080,294 A | * | 6/2000 | Shen et al. |

* cited by examiner

Primary Examiner—Kaj K. Olsen
(74) Attorney, Agent, or Firm—St. Onge Steward Johnston & Reene LLC

(57) ABSTRACT

The invention relates to an electrochemical gas sensor having a substrate, substrate surface for depositing electrodes thereon, counter and sensing electrodes for measuring current flow, an electrolyte for providing an electrical connection between the electrodes, and an electrode surface having minimal porosity, pore size, and thickness for deterring flooding.

24 Claims, 1 Drawing Sheet

ELECTROCHEMICAL SENSORS HAVING NONPOROUS WORKING ELECTRODE

FIELD OF THE INVENTION

The invention relates to an apparatus and method for an electrochemcial sensor having an electrode comprising a thin film and, more particularly, an electrode having a minimal porosity

BACKGROUND OF THE INVENTION

Monitoring toxic gases is a great concern in relation to environmental pollution, occupational health, and industrial emission control. Known methods and apparatuses have been developed to detect the presence of gases. For example, gas chromatography, ion chromatography, electrolytic conductivity detection, and conductometric measurement are typically used to detect gases. However, these manners for detecting gases have generally been expensive and cumbersome.

Electrochemical sensors were provided to overcome these limitations. Electrochemical sensors typically operate at room temperature, provide a signal which varies linearly with concentrations of analyte species, have short response time, and exhibit acceptable sensitivity with high durability. In addition, electrochemical sensors are compact and can be used for continuous monitoring.

Known electrochemical gas sensors typically include gas diffusion electrodes in contact with a conductive medium, such as electrolyte. Sensors typically measure gas by diffusing it through an electrolyte. The electrolyte is in contact with electrodes, which in turn permits a measurement of current flow between them. The gas generally undergoes either oxidation or reduction to produce yielding a signal in the form of a current, which is typically larger than the background current. Hence, there is generally a correlation between a measurement of current flow and the concentration of a particular gas.

The cornerstone of these sensors generally has been on optimizing the electrode/gas/electrolyte interface in order to achieve higher sensitivity. However, known sensors having thick films of electrolyte require longer gas diffusion times and, therefore, have slower response times.

Recently, planar thin film sensors have been developed by constructing three planar electrodes on alumina substrate and covering them with a thin polymer electrolyte, such as Nafion. J. A. Cox and K. S. Alber, *Amperometric Gas Phase Sensor for the Determination of Ammonia in a Solid State Cell Prepared by a Sol-Gel Process*, 143, No. 7 J. Electrochem. Soc. L126–L128 (1996) developed a solid state cell in which microelectrode arrays were coated with a film of vanadium oxide xerogel for detection of ammonia. However, this film needs to be soaked in a solution in order to provide ionic conductivity. Soaking the electrolyte tends to cause a thick layer of electrolytic solution, which floods the electrode surface. Flooding negatively affects sensor response time due to the thick layer of electrolytic solution through which gas must diffuse.

Another contributor to flooding is an electrode surface having crevices or pores, where electrolytic solution may accumulate. Because a difference of only a fraction of a micrometer differentiates between a desirably thin film of electrolyte and a thick film of electrolytic solution that floods the electrodes, crevices or pores in the surface may affect sensor sensitivity. Similarly, wicking, where solution seeps into or beneath the electrode surface, negatively affects sensor response time for the same reasons as crevices/pores.

Lower temperatures may also negatively affect an electrochemical sensor's efficiency for the response time is typically slower. This may be due to a host of factors, including a higher viscosity of the solution used to wet the electrolyte.

U.S. Pat. No. 5,716,506 to Maclay et al. ("Maclay") relates to an electrochemical gas sensor for detecting gases and taking into account relative humidity and air temperature. The patent discloses thin film platinum electrodes for increasing a sensor's sensitivity. The patent also discloses that the electrodes may be electrodeposited, or electroplated in acid. The reference further discloses that electrodes may be sputtered onto a substrate. However, nowhere does Maclay disclose an electrode comprising a thin film for minimizing flooding of the working electrode. Also, Maclay does not disclose an electrode surface that minimizes crevices or porosity for preventing flooding and/or wicking. Further, nowhere does Maclay disclose an acidic solution for use in a sensor operating below 0° C.

What is desired, therefore, is an electrochemical sensor having improved sensitivity and response time. What is also desired is a sensor that prevents flooding and/or wicking of the electrode surface. What is further desired is a sensor operational at lower temperatures.

SUMMARY OF THE INVENTION

Accordingly, it is an object of the invention to provide an electrochemical gas sensor having an electrode surface free from pores or crevices.

It is another object of the invention to provide an electrochemical gas sensor having an electrode that deters wicking.

It is also an object of the invention to provide an electrochemical gas sensor having an electrode that deters flooding.

It is yet another object of the invention to provide an electrochemical gas sensor having consistent sensitivity whether operating above or below 0° C.

Still another object of the invention is to provide an electrochemical gas sensor having improved sensitivity and response time by maximizing the quantity of interfaces between gas, electrode, and electrolyte.

These and other objects of the invention are achieved by an electrochemical gas sensor having a substrate, substrate surface for depositing electrodes thereon, counter and sensing electrodes for measuring current flow, an electrolyte for providing an electrical connection between the electrodes, and an electrode surface having a predetermined porosity, pore size, and thickness for deterring flooding.

The electrode surface may further have a porosity of between 2% and 5% or, preferably, less than 1%. The lower the porosity, the less likely flooding will occur. A nonporous surface is ideal for then electrolyte could not gather in the crevices, thereby contributing to flooding.

The electrode surface may further have a pore size of between 0.05 and 0.12 micrometers at a pore's greatest measurement or, preferably, less than 0.01 micrometers. The smaller the pore size, the less likely flooding will occur. A nonporous surface is ideal for then electrolyte could not gather in the pores, thereby contributing to flooding.

The electrode surface may further have a thickness of between and 0.2 and 1 micrometers or, preferably, less than 0.1 micrometers for the thinner the electrode, the less likely pores or crevices will form in the electrode. An ideal thickness would be such that a nonporous electrode surface is formed for the electrode would lack the necessary depth to permit a pore or crevice to completely form.

Another aspect of the electrochemical gas sensor includes an acidic solution for hydrating the dry or solid state electrolyte. The acidic solution enables the sensor's response time and sensitivity to be consistent in lower temperatures and, more specifically, below 0° C. The sensor may further include a reservoir for containing the solution used to hydrate the electrolyte.

The invention and its particular features and advantages will become more apparent from the following detailed description considered with reference to the accompanying drawings.

DETAILED DESCRIPTION OF THE DRAWINGS

Figure 1:
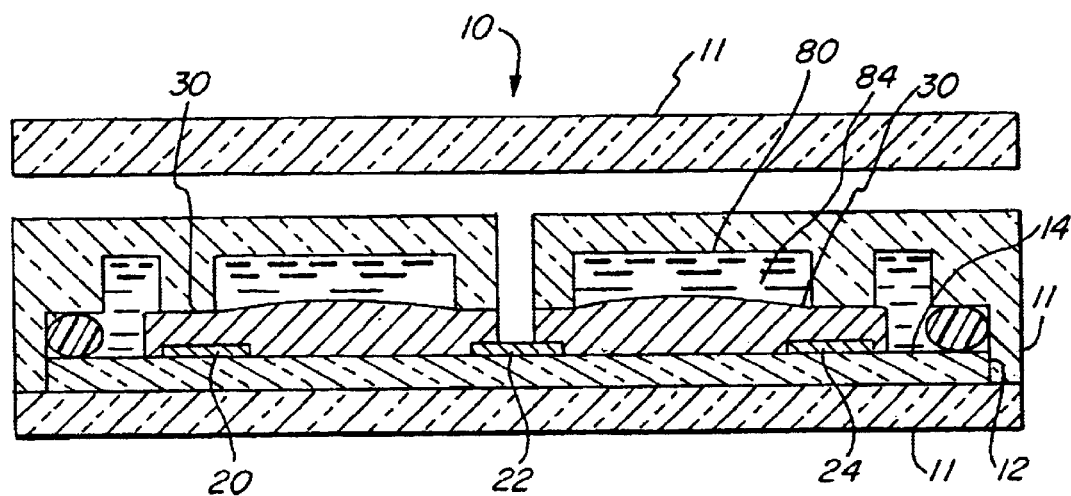
FIG. 1 depicts the electrochemical gas sensor in accordance with the invention.

FIG. 1 depicts the electrochemical gas sensor 10 in accordance with the invention. Electrochemical gas sensor 10 comprises housing 11, substrate 12, surface 14 of substrate 12, electrolyte 30, first electrode 20, and second electrode 22. Electrochemical gas sensor 10 may also include third electrode 24. Electrochemical gas sensor 10 operates to detect the presence of a particular gas in an unknown mixture of gases.

Substrate 12 includes known or novel materials used for forming a supporting surface 14 upon which the electrodes are placed. The substrate has a surface that has a porosity of less than 25% and a pore size of less than 15 micrometers at a pore's greatest distance. Preferably substrate 12 has a porosity less than 5% and a pore size less than 0.15 micrometers. Substrate 12 having the above-mentioned characteristics generally permits a film of electrode material to be deposited in a manner that has a porosity of less than 5% and a pore size not exceeding the smaller of either a width or length of the film at a pore's greatest measurement. The reason for such a generally flat surface is so that desirably thin film electrodes may be deposited thereon free from unnecessary pores or crevices, thereby reducing wicking and porosity, both of which disadvantageously affect sensor sensitivity. Substrate 12 ideally has no porosity so as to provide an ideally flat surface upon which electrodes are deposited. It is also desired for the electrodes to likewise have a porosity of less than 25% and, preferably, less than 5%. The electrodes' pore size are less than 15 micrometers and, preferably, less than 0.15 micrometers at a pore's greatest distance. Most preferably, the electrodes are deposited in a manner that has a porosity of less than 5% and a pore size not exceeding the smaller of either a width or length of the electrode at a pore's greatest measurement. Ideally, the electrodes have no porosity. However, such electrode requirements will not be met unless substrate 12 upon which the electrodes are deposited is also subjected to similar standards of porosity and pore size.

Suitable substrate materials include glass or any electrically insulating material. Substrate 12 and surface 14 should be made of a material that is a poor conductor of electricity so as not to interfere with proper functioning of electrochemical gas sensor 10. Such a material may be classified as an insulating material.

Housing 11 may, but need not, be of the same material as substrate 12. Housing 11 includes known or novel materials used in the art for making electrochemical gas sensors.

First and second electrodes, 20 and 22, are essential for proper functioning of electrochemical gas sensor 10. A measurement of current is taken between first and second electrodes, 20 and 22. Electrolyte 30 is in contact with both first and second electrodes and acts as a conductive medium to carry current in the form of ions between first and second electrodes, 20 and 22. It should be known that current may flow to or from either electrode and that first and second electrodes are interchangeable. Hence, either electrode may act as a sensing or counter electrode, depending on the direction of the flow of current. For pictorial and exemplary purposes only, first electrode 20 is the counter electrode and second electrode 22 is the sensing electrode.

When an unknown gas mixture comes into contact with electrochemical gas sensor 10 it undergoes oxidation or reduction and increases the current flow between the electrodes. For the sensor to function, the unknown mixture must diffuse through the electrolyte to the sensing electrode, where the gas sensing occurs. The thickness of the electrolyte film determines the sensor response time and sensitivity; the thicker the electrolyte film, the slower the response and the lower the sensitivity.

First electrode 20 includes any electrically conductive material for permitting current measurement. Generally, a metallic material, such as platinum, is used for these types of materials provide sufficient conductivity. However, any known or novel material suffices so long as it is electrically conductive for permitting a measurement of current.

Second electrode 22 includes all the limitations of first electrode 20, including an ideally nonporous and non-wicking surface or a surface having negligible porosity and/or wicking. Having both electrodes made of the same material is best for conductivity but need not be required for proper functioning of sensor 10. First electrode 20 being of a different material than second electrode 22 still permits sufficient conductivity and efficiency.

Second electrode 22 is desirably thin, such as a thickness less than 10 micrometers and, preferably, less than 1 micrometer, so as to reduce wicking and porosity, both of which are undesirable and negatively affect response time and sensor sensitivity. Second electrode 22 is deposited in a manner that has a porosity of less than 5% and a pore size not exceeding the smaller of either a width or length of second electrode 22 at a pore's greatest measurement. When the electrode is a thin film, essentially any crevice or pore formed in the electrode surface would in fact be a hole all the way through the electrode for the thin film lacks the depth necessary to completely form a crevice or pore. Hence, second electrode 22 is ideally nonporous and non-wicking or having negligible porosity and/or wicking. The invention does not require first electrode 20 or third electrode 24 to have a thickness similar to second electrode 22 for sensor 10 to function properly.

In addition, electrochemical gas sensor 10 may further include third electrode 24 deposited on surface 14. Third electrode 24 is not necessary for proper functioning of electrochemical gas sensor 10 but provides a more desirable sensor for sensitivity, accuracy, selectivity, and/or repeatability are improved. If first electrode 20 operates as the counter electrode and second electrode operates as the sensing electrode, third electrode 24 functions as a reference electrode which helps in controlling the potential of working electrode independent of counter electrode potential. Third electrode 24 includes all the limitations of both first and second electrodes, 20 and 22, and may further be interchanged with either of first and/or second electrode, 20 and/or 22. However, for the purposes of FIG. 1, third electrode 24 is depicted as the reference electrode.

Electrolyte 30 is a conductive medium for carrying a flow of current between first and second electrodes, 20 and 22. Electrolyte 30 also carries a current between third electrode 24, if applicable, and either first or second electrode. Electrolyte 30 further includes a conductive medium in the solid state, such as Nafion.

Solid state electrolyte is advantageous in that it permits the thickness of the electrolytic layer to be less than an electrolytic layer in a liquid state. Generally, electrolyte 30 is between 1–1000 micrometers thick An electrolyte having this thickness permits quicker gas diffusion and quicker sensor response time. However, if solid state or dry electrolyte is used, it needs to be wetted in order for sensor 10 to function properly. Dry electrolyte is known to have poor electrically conductive properties.

Hence, solution 84 functions to improve the sensor's sensitivity by wetting electrolyte 30. Solution 84 includes liquid electrolyte, water, or an acid solution. Solution 84 is contained in reservoir 80 within the sensor. However, a controlled wetting is desired for flooding of the electrodes causes the sensor to malfunction. Flooding the electrodes with solution 84, particularly at the sensing electrode's surface, negatively affects sensor sensitivity and response time, as mentioned above.

Empirical data suggests that the composition of solution 84 affects the functionality of sensor 10 in lower temperature environments. At room temperature, at or about 25° C., or higher, solution 84 may comprise of water, liquid state electrolyte, an acidic solution, or other solution for wetting solid state electrolyte 30.

However, at temperatures below 0° C., the composition of solution 84 becomes more important. Solution comprising an acidic solution provides better sensor performance than water. Therefore, sensor 10 includes an acidic solution when operating in an environment below 0° C.

Figure 2:
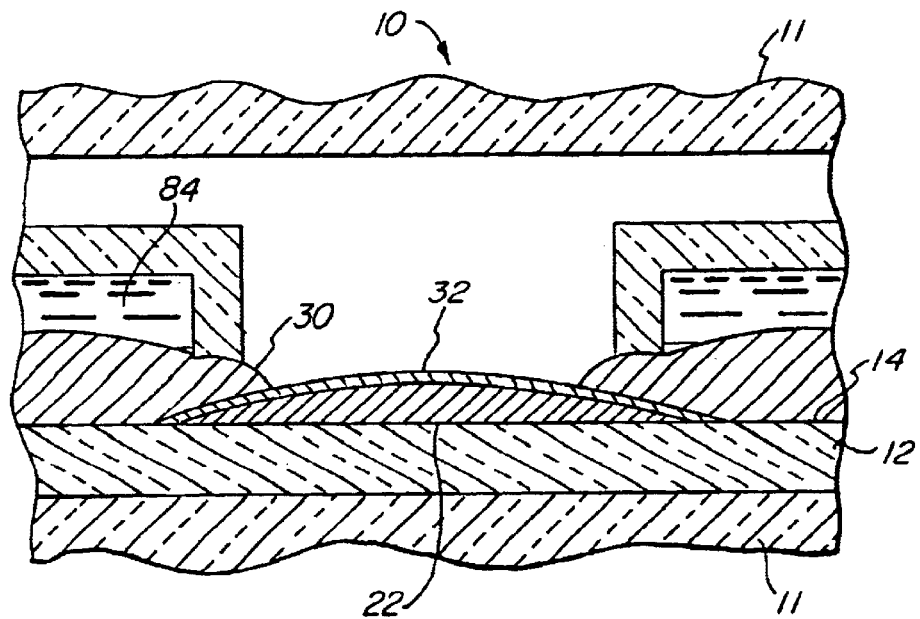
FIG. 2 depicts the sensing electrode having a thin layer of electrolyte on the surface for increasing the quantity of interfaces between gas, electrode, and electrolyte.

Electrolyte 30 further includes layer 32 on second electrode 22. Layer 32 is more specifically depicted in FIG. 2. The purpose of layer 32 is to increase the quantity of interfaces between gas, electrolyte, and electrode to include the surface of sensing electrode 22 for gas diffuses throughout layer 32, which is in contact with the surface of sensing electrode 22. Without layer 32, the interface in the approximate area of sensing electrode 22 would be substantially smaller, limited to an area where electrolyte 30 comes in contact with sensing electrode 22. This contact area would generally be a linear contact point defining an approximate circumference of the electrode.

Layer 32 further has a thickness less than 2 micrometers, such that gas diffusion time is minimized. Ideally, layer 32 should be as thin as possible to maximize sensor sensitivity. Hence, sensor 10 may further comprise layer 32 having a thickness of less than 1 micrometer. An electrolyte having such reduced thickness permits faster gas diffusion and, thus, faster response times. Layer 32 is an electrolytic medium including all the limitations of electrolyte 30 and may be, but need not be, the same material as electrolyte 30.

Layer 32 is in a solid state or dry electrolyte for it has more structural integrity than liquid state electrolyte, thereby permitting a consistently uniform thickness over sensing electrode 22. This enhances sensor repeatability and facilitates functionality for liquid state electrolyte would be difficult to maintain in a fixed position on the surface of sensing electrode 22.

Although the invention has been described with reference to a particular arrangement of parts, features and the like, these are not intended to exhaust all possible arrangements or features, and indeed many other modifications and variations will be ascertainable to those of skill in the art.

What is claimed is:

1. An electrochemical gas sensor, comprising:
    a substrate having a surface;
    a first electrode deposited on said surface;
    a second electrode spaced apart from said first electrode and deposited on said surface for detecting a gas;
    an electrolytic material in electrical contact with said first electrode and said second electrode for carrying a flow of current;
    said second electrode having a porosity of less than 5%, a pore size less than 0.12 micrometer at said pore size's greatest measurement, and a thickness less than 0.2 micrometer for controlling flooding; and
    a reservoir for containing a solution to hydrate said electrolyte.

2. The electrochemical gas sensor according to claim 1, wherein said porosity is less than 2%.

3. The electrochemical gas sensor according to claim 1, wherein said pore size is less than 0.05 micrometer at said pore size's greatest measurement.

4. The electrochemical gas sensor according to claim 1, wherein said porosity is less than 1%.

5. The electrochemical gas sensor according to claim 1, wherein said pore size is less than 0.01 micrometer at said pore size's greatest measurement.

6. The electrochemical gas sensor according to claim 1, wherein said thickness is less than 0.1 micrometer for deterring flooding.

7. The electrochemical gas sensor according to claim 1, wherein said second electrode has negligible porosity.

8. The electrochemical gas sensor according to claim 1, wherein said second electrode is nonporous.

9. The electrochemical gas sensor according to claim 1, wherein said first electrode is sputter coated.

10. The electrochemical gas sensor according to claim 1, wherein said first electrode is vapor deposited.

11. The electrochemical gas sensor according to claim 1, wherein said second electrode is sputter coated.

12. The electrochemical gas sensor according to claim 1, wherein said second electrode is vapor deposited.

13. The electrochemical gas sensor according to claim 1, further including an acidic solution for hydrating said electrolyte.

14. The electrochemical gas sensor according to claim 1, wherein each pore of said second electrode is less than 0.12 micrometer at its greatest measurement.

15. The electrochemical gas sensor according to claim 1, wherein said substrate has a pore less than 0.05 micrometer at its greatest measurement.

16. The electrochemical gas sensor according to claim 1, wherein said substrate has a pore less than 0.01 micrometer at its greatest measurement.

17. The electrochemical gas sensor according to claim 1, wherein said surface of said substrate has negligible porosity.

18. The electrochemical gas sensor according to claim 1, wherein said surface of said substrate is generally flat.

19. The electrochemical gas sensor according to claim 1, wherein said surface of said substrate has a porosity of less than 5%.

20. The electrochemical gas sensor according to claim 1, wherein said surface of said substrate has a porosity of less than 20%.

21. The electrochemical gas sensor according to claim 1, wherein said surface of said substrate has a porosity of less than 1%.

22. The electrochemical gas sensor according to claim 1, wherein said electrolytic material includes:

an acidic solution for hydrating said electrolyte.

23. The electrochemical gas sensor according to claim 22, wherein said acidic solution is 30% acidic.

24. The electrochemical gas sensor according to claim 22, wherein said acidic solution is 50% acidic.

* * * * *